(12) United States Patent
Eifler

(10) Patent No.: US 11,305,081 B2
(45) Date of Patent: *Apr. 19, 2022

(54) MASK BEAD FOR A PATIENT INTERFACE

(71) Applicant: Loewenstein Medical Technology S.A., Luxembourg (LU)

(72) Inventor: Martin Eifler, Glueckstadt (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 547 days.

This patent is subject to a terminal disclaimer.

(21) Appl. No.: 16/211,702

(22) Filed: Dec. 6, 2018

(65) Prior Publication Data

US 2019/0167933 A1    Jun. 6, 2019

Related U.S. Application Data

(63) Continuation of application No. 14/090,779, filed on Nov. 26, 2013, now Pat. No. 10,166,354.

(30) Foreign Application Priority Data

Nov. 29, 2012    (DE) .......................... 102012023268.3

(51) Int. Cl.
   *A61M 16/06*    (2006.01)

(52) U.S. Cl.
   CPC ........ *A61M 16/06* (2013.01); *A61M 16/0616* (2014.02)

(58) Field of Classification Search
   CPC .................. A61M 16/06; A61M 16/0616
   See application file for complete search history.

(56) References Cited

U.S. PATENT DOCUMENTS

| 2008/0110464 A1* | 5/2008 | Davidson | A61M 16/06 128/206.26 |
| 2009/0145429 A1* | 6/2009 | Ging | A61M 16/0875 128/202.27 |
| 2010/0313891 A1* | 12/2010 | Veliss | A61M 16/0622 128/206.26 |

* cited by examiner

*Primary Examiner* — Margaret M Luarca
(74) *Attorney, Agent, or Firm* — Abel Schillinger, LLP

(57) ABSTRACT

Disclosed is a mask bead for a patient interface that comprises a contact area, a nose bridge area having a width (B1), side areas, a base area, and a bearing area on a patient. The bearing area extends from the side areas, the base area and the nose bridge area to a central opening is being designed as a sealing lip which frames the central opening. The mask bead further has a maximum width (B2), the ratio B1 to B2 being one to three or greater.

20 Claims, 7 Drawing Sheets

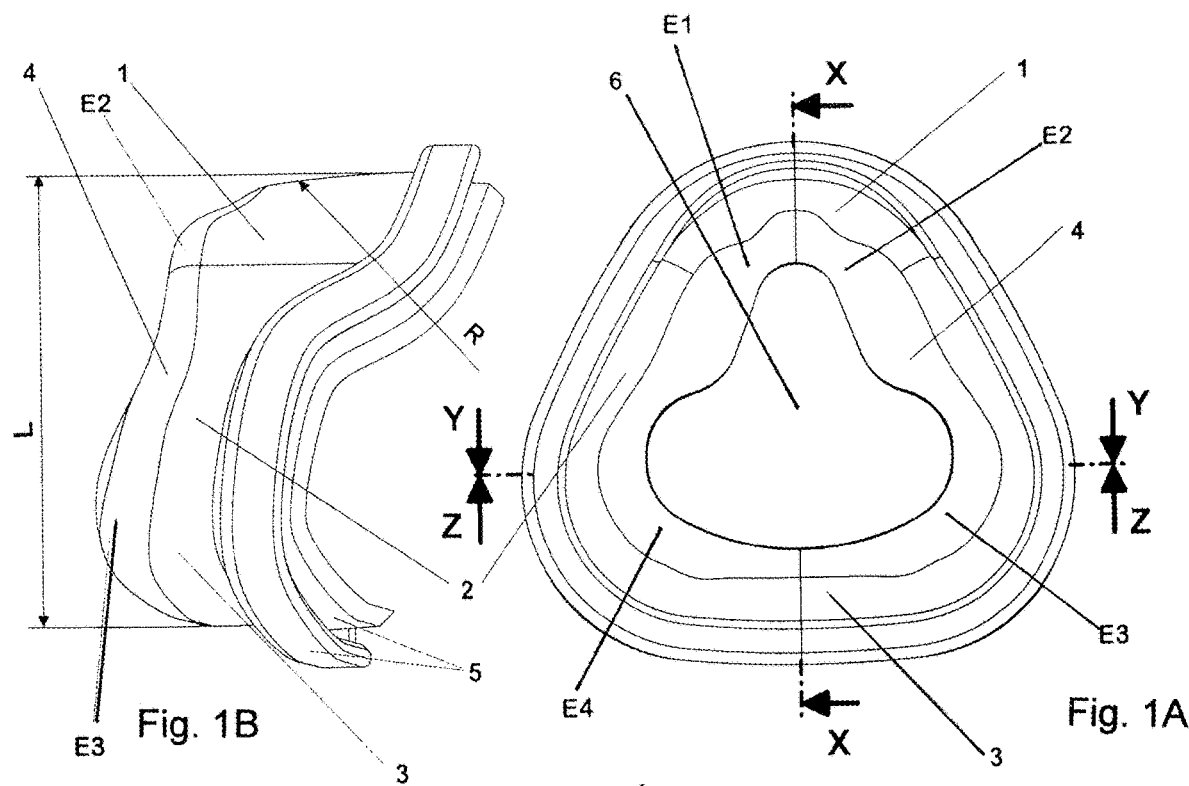
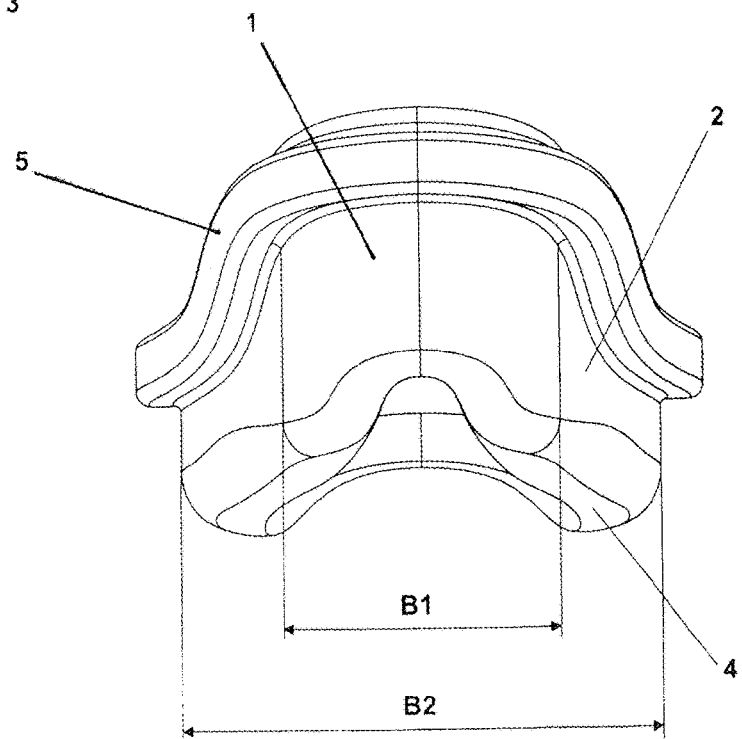

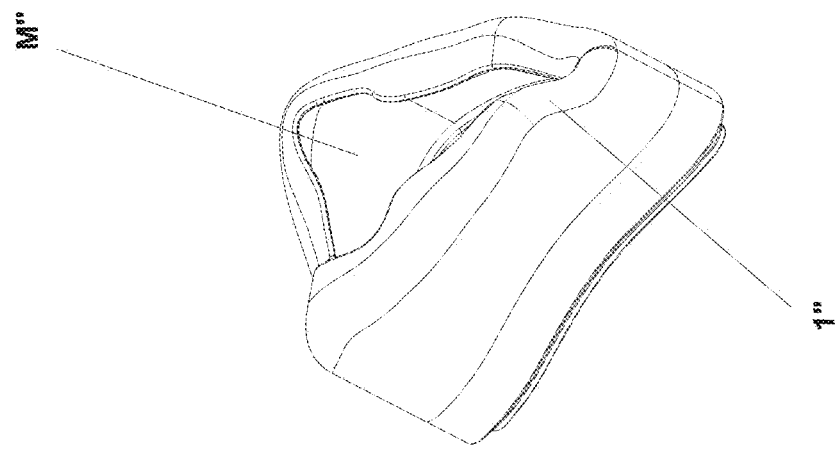
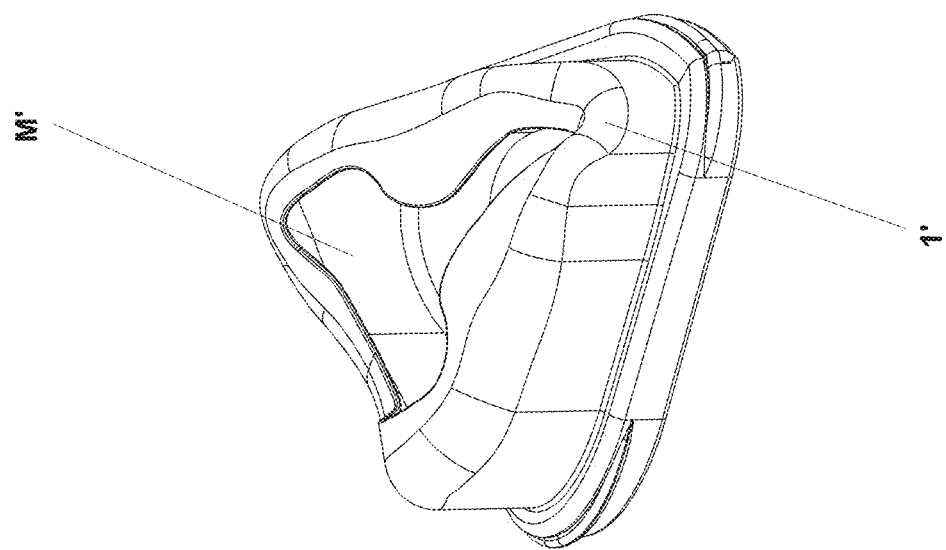
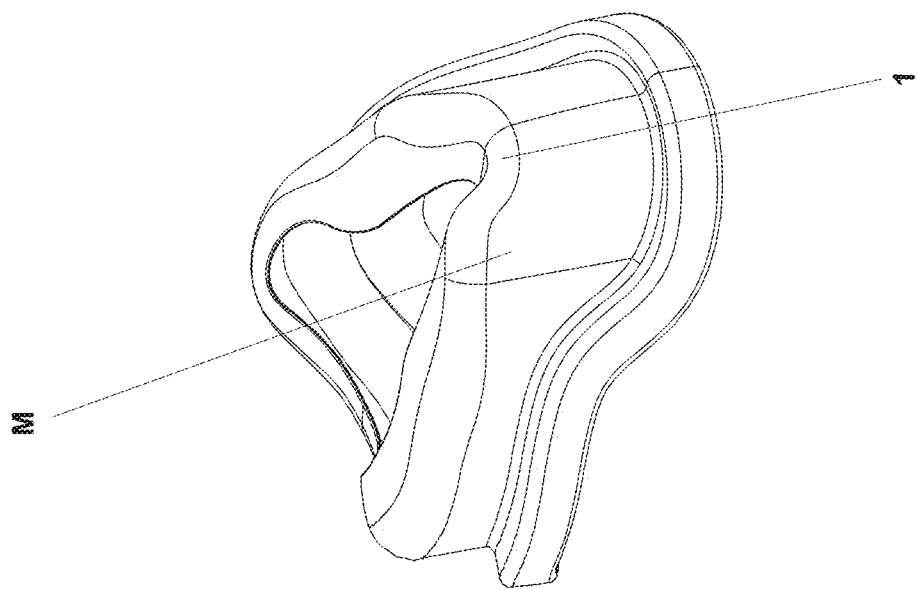
Fig. 3

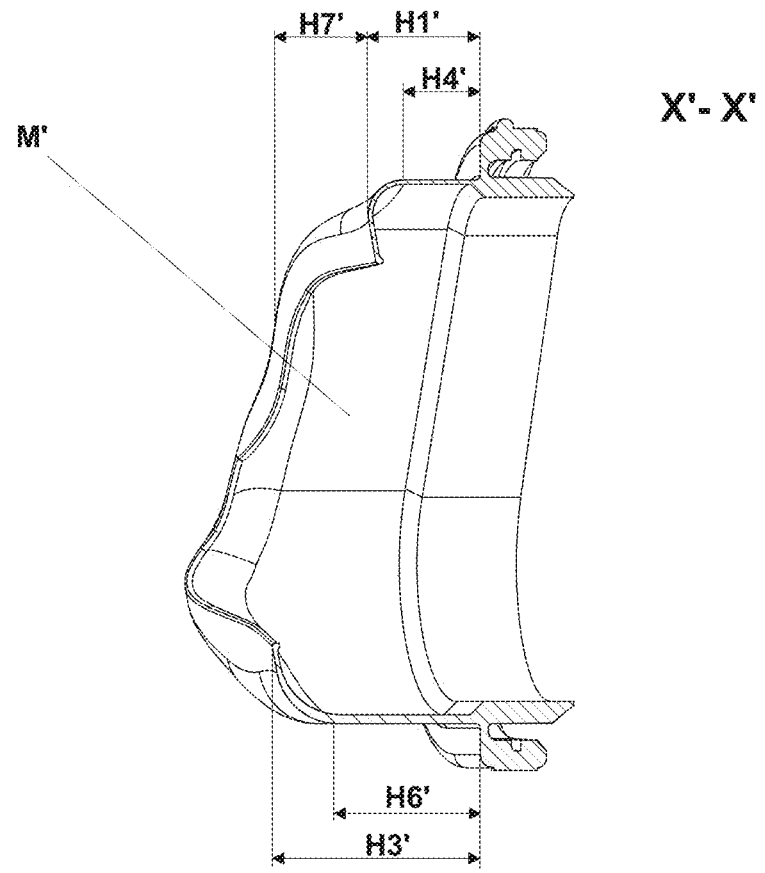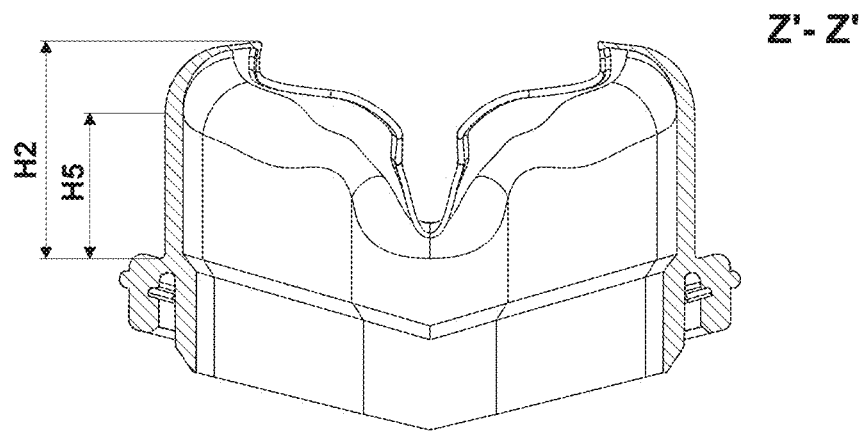
Fig. 5

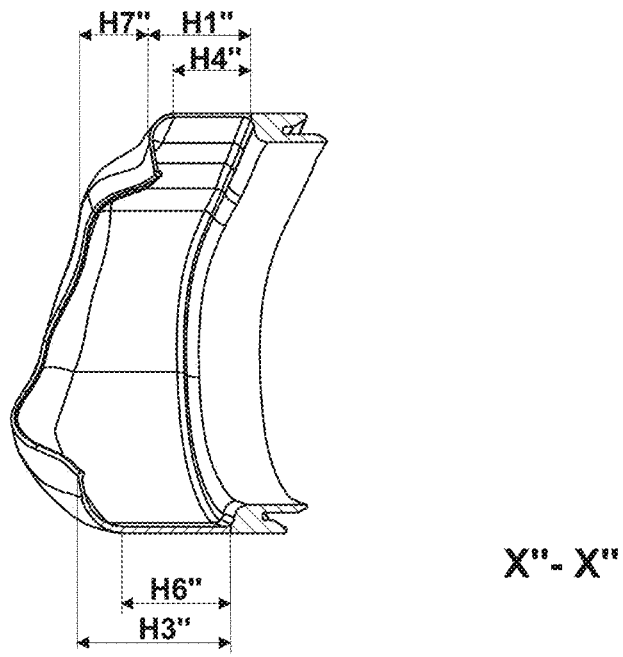
X"- X"
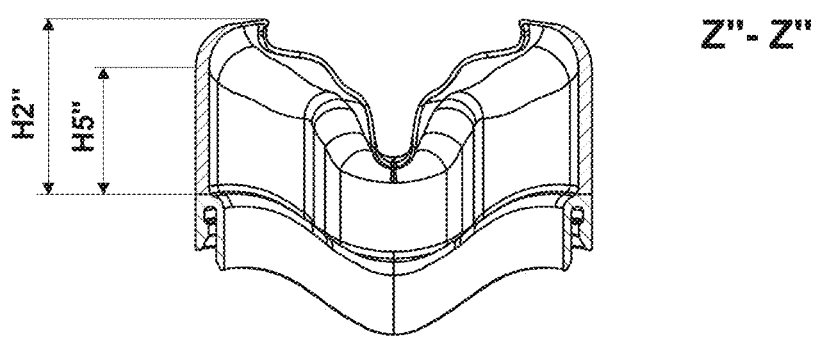
Z"- Z"
Fig. 7

MASK BEAD FOR A PATIENT INTERFACE

CROSS-REFERENCE TO RELATED APPLICATIONS

The present application is a continuation of U.S. patent application Ser. No. 14/090,779, filed Nov. 26, 2013, which claims priority under 35 U.S.C. § 119 of German Patent Application No. 10 2012 023 268.3, filed Nov. 29, 2012. The entire disclosures of these applications are expressly incorporated by reference herein.

BACKGROUND OF THE INVENTION

1. Field of the Invention

The present invention relates to a mask bead for a patient interface.

2. Discussion of Background Information

Masks are used in the area of respiration and sleep therapy for supplying a patient with respiratory gas by means of a flow or pressure source. The mask represents the interface between patient and appliance. It consists in most cases of a mask body with a mask bead and is fixed on the patient's head by means of a harness and, optionally, an additional forehead support. The mask body is generally made of a relatively stiff plastic, and the mask bead, which bears on the face or on parts of the face of the patient, is made of a relatively thin, soft material, preferably a skin-compatible silicone, a thermoplastic elastomer (TPE) or polyurethane, and it generally has a sealing lip in order to ensure a sufficient seal and to prevent leaks.

Most conventional mask beads for a breathing mask are usually available in the sizes S, M and L, so as to meet the greatest possible number of different configurations of the face and nose of the patients, and so as to ensure the greatest possible wearing comfort, the best possible fit, and a high degree of leaktightness.

Known solutions of this kind mean that a large number of masks have to be offered in order to cover all different shapes and sizes of faces.

It would be advantageous to have available a mask bead that is suitable for nasal masks and/or full-face masks and that provides a high degree of adaptability to different sizes and different shapes of face parts and nose parts of the patients. Patients can have different nose shapes with high or low nose bridge regions, narrow or broad and long or short noses. The mask bead should therefore be able to adapt to all possible nose shapes and to provide the desired fit and leaktightness.

SUMMARY OF THE INVENTION

The present invention provides a mask bead for a patient interface which comprises (e.g., consists of) a contact area to the mask body, a nose bridge area bearing on the nose bridge and with a width (B1), side areas, a base area, which in the case of a nasal mask lies on the upper lip under the nostrils and in the case of full-face masks bears on the chin, and a bearing area on the patient, which assumes the actual sealing function, wherein the bearing area extends from the side areas and the base area and the nose bridge area to the opening, and wherein the bearing area is designed as a sealing lip, preferably a single sealing lip, which frames the central opening serving at least for the introduction of the nose of the patient, wherein the mask bead has a width (B2), and wherein the ratio of the widths B1 to B2 is one to three or greater. The ratio of the widths B1 to B2 is preferably one to two or greater. Masks from the prior art have a ratio of the widths B1 to B2 of about one to four.

In one aspect of the mask bead according to the invention, a wall thickness (W1) of ≤0.6 mm may be used in the nose bridge area.

In another aspect, the nose bridge area may have a width (B1) in the range of 27-37 mm.

In yet another aspect, the height (H1) in the nose bridge area may be in the range of 17-27 mm, preferably 20-25 mm.

In a still further aspect of the mask bead, the height (H4) in the nose bridge area may be in the range of 14-23 mm.

In another aspect, the nose bridge area has an arc-shaped contour (R) with an angle α in the range greater than 90°.

In another aspect of the mask bead according to the invention, the base area may have a wall thickness (W3) in the range of 0.8-1.2 mm.

In another aspect, the height (H3) of the base area may be in the range of 16-21 mm.

In another aspect, the height (H6) of the base area may be in the range of 8.5-13.5 mm.

In another aspect of the mask bead, the side area may have a wall thickness (W2) in the range of 1.5-2.8 mm.

In another aspect, the height (H2) of the side area may be in the range of 12-22 mm, preferably in the range of 14-16 mm.

In another aspect, the height (H5) of the side area may be in the range of 6-14 mm.

In another aspect of the mask bead according to the invention, the wall thickness in the side area may decrease continuously from the base (W2) toward the bearing area (W4).

In another aspect, the bearing area may have an approximately constant wall thickness (W4) in the range of 0.2-0.75 mm.

In another aspect, the ratio of the length (L) of the mask bead to the width (B2) may be approximately 1 to 1.

In another aspect, the width (B2) may be approximately in the range of 54 mm to 65 mm.

The present invention also provides a mask bead for a patient interface which comprises (e.g., consists of) a contact area, a nose bridge area with a width (B1), a maximum width of the mask bead (B2), side areas, the base area, and the bearing area on the patient, wherein the bearing area extends from the side areas and the base area and the nose bridge area to the opening, and wherein the bearing area is designed as a sealing lip which frames the central opening serving at least for the introduction of the nose of the patient. The bearing area, at the transitions from nose bridge area to side area and from base area to side area, has corner points (E1-E4), which serve to align the mask on the face.

In one aspect of the above mask bead according to the invention, the lower corner points (E3, E4) may be located on both sides of the plane of symmetry (x-x) and serve to align the bead on the nasolabial groove.

In another aspect, the upper corner points (E1, E2) may lie in the area to the sides of the nose and define the end of the support area and, therefore, the transition to the nose bridge area with the width (B1).

In yet another aspect of the mask bead according to the invention, the material of the mask bead may have an extensibility (stretchability) of more than 800%.

In a still further aspect, the bead may have been produced in a two-component process.

In order to cover a wide range of very different nose sizes and shapes, a mask bead is proposed which in terms of length lies in the size range of a mask of size S and in terms of width lies in the size range of a mask of size M. This gives the mask bead a ratio of length (L) to width (B2) of approximately 1:1. For attachment to the mask body, use is made, for example, of a peripheral U-shaped holding profile as contact area, which has an inner branch and an outer branch with an undercut and latches onto the mask body via a peripheral edge. For exact positioning, use is made of transverse webs in the holding profile of the mask bead, which transverse webs have to be fitted into grooves in the mask body. However, it is also possible to connect the mask bead to the mask body in the contact area by means of two-component processes.

To achieve a high degree of adaptability to different sizes and different shapes of nose parts of a patient, the mask bead has, in the nose bridge area, a very broad form (B1) with a very large, thin-walled area that is easily deformable.

The adaptability to different sizes and different shapes of nose parts of the patients is manifested in particular in the special design of the nose bridge area. From the comparison between the invention and the prior art, it is clear that, in the bead according to the invention, it is not only the ratio B1 to B2 that differs from the prior art, but also the ratio H1 to H2. According to the invention, H1 is always the same as or greater than H2. In masks from the prior art, H1 is always smaller than H2.

The invention is applicable to elastic mask beads which are secured releasably or permanently on a hard mask body, and likewise to mask beads that are made entirely from an elastic material. Mask beads that are made entirely from an elastic material then have, instead of the hard mask body, either a hard mask frame, into which the mask bead is fitted, or a thickened or stiffened portion that assumes the supporting function of the hard mask body. The contact area to the mask body is then generally the region where the elastic mask bead merges into a thickened or stiffened portion or is supported by the mask frame.

The mask bead may be made from a comfortable, skin-compatible material, preferably silicone in a Shore hardness range of 35 to 55 Shore A, preferably of 40-50 Shore A.

The mask bead can be produced in a two-component process, wherein the bead is produced from a soft material and is preferably injected onto a hard material. The hard material defines the contact area or the mask body or a part of the bead with supporting function. In the latter case, the bead is produced in two parts from a soft material and a hard material. The contact is preferably obtained by adhesion of the materials. Alternatively or additionally, mechanical contact points can strengthen the adhesion (positive locking).

The bead according to the invention can also have a hollow space that has a resilient filling material. The hollow space is preferably designed about the periphery. In an alternative embodiment, there is no filled hollow space in the nose bridge area. The filling material can be a gel or foam or gas or a liquid or a soft filler. A gel would be introduced in the liquid state into the hollow space and would harden there. The filling material preferably has a hardness in the range of 2 Shore A to 20 Shore A, preferably in the range of 2 Shore A to 10 Shore A, particularly preferably in the range of 10 Shore A to 20 Shore A. The filling can also have varying hardness: softer near the face, harder away from the face.

The mask bead is preferably made from silicone or PU (polyurethane). The material of the mask bead has an extensibility which preferably is in the range of more than 500%, more preferably more than 800%, particularly preferably more than 1000%.

BRIEF DESCRIPTION OF THE DRAWINGS

In the drawings:

FIG. 1A shows a mask bead (M) in a plan view
FIG. 1B shows a mask bead (M) in a side view
FIG. 1C shows a mask bead (M) from above
FIG. 3 shows a comparison between the invention and the prior art, with perspective views of mask beads (M), (M') and (M")
FIG. 5 shows sectional views of the mask bead (M')
FIG. 7 shows sectional views of the mask bead (M")

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 2A:
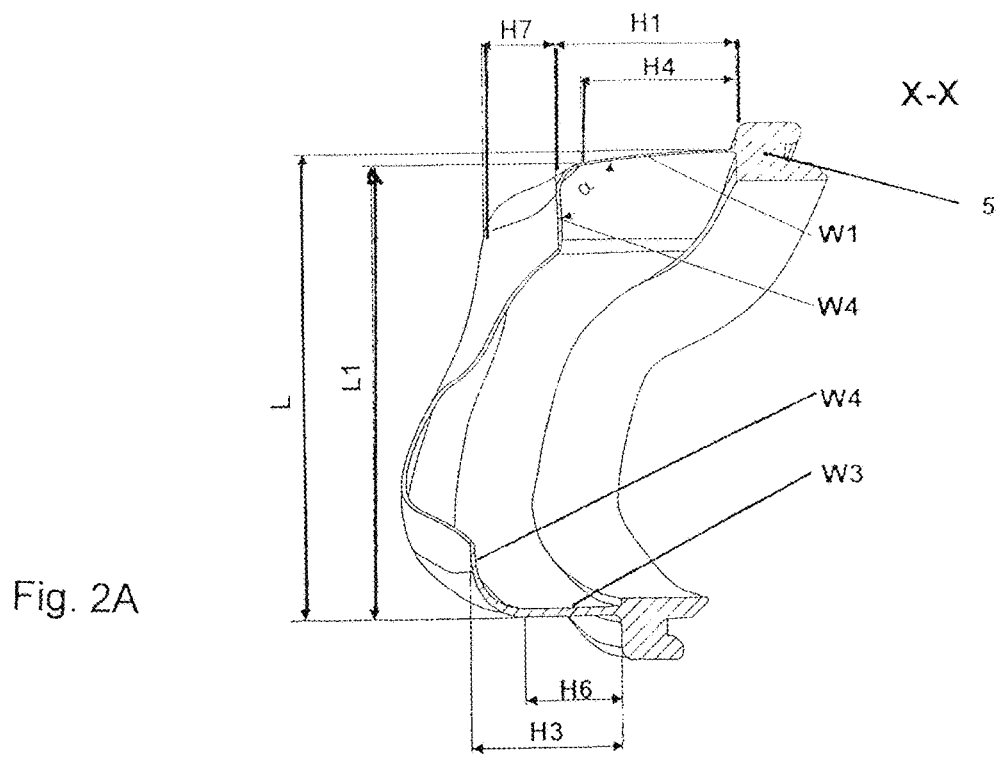
FIG. 2A shows a vertical sectional view of a mask bead (M) along the plane x/x
Figure 2B:
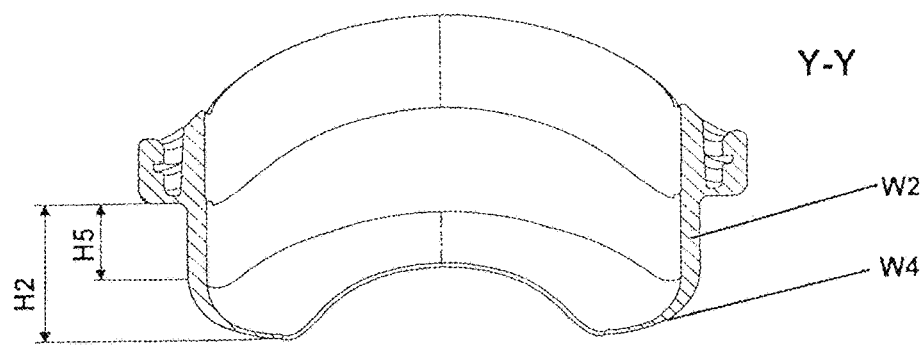
FIG. 2B shows a horizontal sectional view of a mask bead (M) along the plane y/y
Figure 2C:
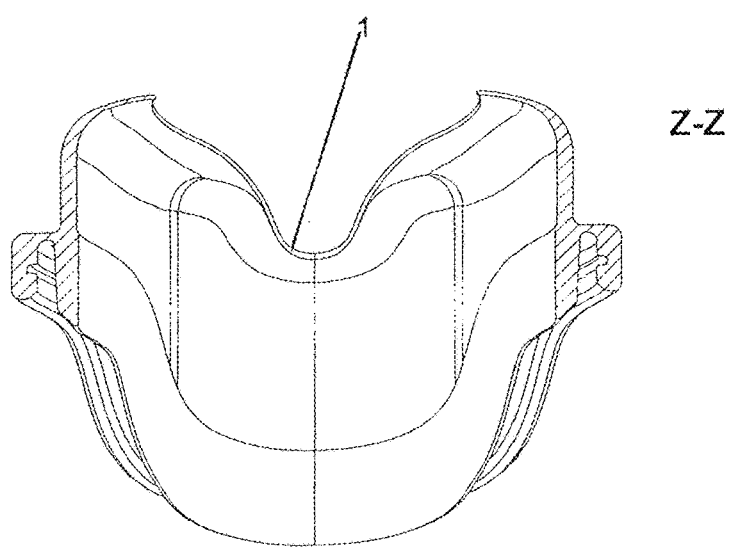
FIG. 2C shows a horizontal sectional view of a mask bead (M) along the plane z/z

FIG. 1A shows the mask bead in a plan view. A vertical sectional plane x and a horizontal sectional plane y/z are plotted. The sections are illustrated in FIGS. 2A-2C. The mask bead has a nose bridge area (1), side areas (2), the base area (3), and the bearing area (4) on the patient. The side areas (2) extend from the contact area to the mask body (5) substantially vertically upward. The bearing area (4) on the patient is designed as a single sealing lip, which is formed integrally onto the other areas and on the inside frees an opening (6) that serves for the introduction of at least the nose of the patient. The bearing area (4) extends in a curve from the side areas (2) and the base area (3) and the nose bridge area (1) to the opening, wherein the bearing area (4) extends at least partially horizontally to the side area (2).

FIG. 1B shows the mask bead in a side view. The patient is most sensitive in the nose bridge area (1), for which reason a very thin wall (W1) of ≤0.6 mm, preferably in the range of 0.25-0.5 mm, is chosen here. The nose bridge area can easily deform and adapt to the shape of the nose. To avoid inward kinking of this area when pressure is applied to the area, an arc-shaped contour (R) was chosen in contrast to the areas (2 and 3) which have a straight contour. The arc in the nose bridge area extends from the contact area to the mask body (5) toward the bearing surface (4). However, it is also possible to have the contour (R) run linearly.

It will also be seen in FIG. 1B that the bead has a contact point to the patient's face, in the area of the thin-walled nose bridge area, and a thin walled upper lip bearing, which are connected by a lateral support area. At the transitions, dominant corner points are obtained that serve to align the mask on the face. The lower corner points (E3, E4) are located on both sides of the plane of symmetry and preferably serve to align the mask on the nasolabial groove. The upper corner points (E1, E2) lie to the sides of the nose (in the area of the maxilla next to the nasal bone) and define the end of the support area and, therefore, the transition to the nose bridge area with the width (B1).

FIG. 1C shows the mask bead in a view from above. The width of the nose bridge area (B1) was chosen to be wider than in known masks, in order to ensure an optimal fit and seal, even in the case of quite broad and also shallow nose shapes. As a result of the chosen geometry, the mask bead sits lower on the nose of the user. With the chosen contour, a high nose bridge engages deeper into the mask bead, but this is not a disadvantage.

In order to cover a wide range of very different sizes and shapes of noses, a mask bead is proposed having a length (L) in the range of 50 mm to 65 mm, preferably of 53 to 62 mm, particularly preferably of 58 mm, and having a width (B2) in the range of 50 mm to 65 mm, preferably of 53 to 63 mm, particularly preferably of 59 mm. This gives a ratio of length (L) to width (B2) of approximately 1:1.

The length (L) lies in the range of a commercially available mask of size S, whereas the width (B2) lies in the range of a mask of size M. The overall proportions of the mask have thus been modified in comparison with the prior art.

The nose bridge area (1) is substantially wider than in the prior art. The width (B1) is in the range of 27-37 mm, preferably of 31 to 35 mm, particularly preferably of 32.5 to 35 mm. The nose bridge area (1) is preferably characterized by a first radius of strong and preferably constant curvature, which merges in the side area into a second radius with a less pronounced curvature or into a substantially straight area (without curvature). The curvature in the side area is preferably half as great as or smaller than in the nose bridge area. Compared to the prior art, the nose bridge area (1) has a thinner wall, with a wall thickness (W1)≤0.6 mm, preferably 0.25 to 0.5 mm.

FIG. 2A shows the bead sectioned in the plane x. The patient is most sensitive in the nose bridge area (1), for which reason a very thin wall (W1) of ≤0.6 mm, preferably of 0.2-0.5 mm, particularly preferably of 0.25 mm, is chosen here. This area can easily deform and adapt to the shape of the nose. To avoid inward kinking of this area when pressure is applied to the area, an arc-shaped contour (R), from the contact area to the mask body (5) toward the bearing surface (4) in the nose bridge area, was chosen in contrast to the areas (2 and 3) which have a straight contour. The angle α measured from the vertical (here illustrated by W4) to the surface of the arc-shaped contour (R) therefore preferably lies in the region greater than 90°, particularly preferably from 91° to 100°. However, it is also possible to have the contour (R) run linearly, and the angle α is then 90°.

In contrast to the side areas (2) with the wall thicknesses (W2), the base area (3) with the wall thickness (W3) is likewise made thin, since a pressure on the jaw is uncomfortable. The wall thickness (W3) is in the range of 0.8-1.2 mm, preferably 1.0 mm. Since the patient is least sensitive at the contact points in the side area (2) of the mask bead, the wall thicknesses (W2) of this area can be made thicker and thus ensure the stiffness and supporting force of the mask bead. In this area, the wall thickness (W2) is 1.5-2.8 mm, preferably 2.1 mm. The bearing area (4) on the patient is designed as a single sealing lip. The bearing area (4) was designed along the entire periphery with an approximately constant, thin wall thickness (W4) of 0.2-0.75 mm, preferably 0.5 mm, which provides the patient with a comfortable fit and additionally serves as a sealing lip.

Mask beads known from the prior art have a double lip, wherein the inner lip is designed as a supporting lip and the outer lip is designed as a sealing lip. The wall thicknesses of the individual areas (1-4) were adapted, according to the invention, to the sensitivity of the contact points in the face of the user. By choosing, according to the invention, different wall thicknesses (W1-W4) for the areas (1-4) of the mask bead, it is possible to do without an additional supporting lip.

The height (H1) in the nose bridge area is 18-27 mm, preferably 20-25 mm, particularly preferably 22.2 mm, and is higher than in masks from the prior art. In this way, a wide area is obtained with good sealing properties for different nose bridges.

The height (H4) in the nose bridge area is higher than in commercially available mask beads and is in the range of 14-23 mm, preferably 18.9 mm.

The height (H3) of the base area (3) is less than in commercially available mask beads and is in the range of 16-21 mm, preferably 18.5 mm.

The height (H6) of the base area (3) is likewise less than in commercially available mask beads and is in the range of 8.5-13.5 mm, preferably 11.9 mm, and has a supporting function. The height (H7) (difference between the nose bridge bearing and the bearing in the side area) corresponds substantially to the heights of the masks from the prior art.

FIG. 2B shows the bead sectioned in the plane y. The height (H2) of the side area (2) is less than in commercially available mask beads and is in the range of 12-22 mm, preferably 15.8 mm. The height (H5) of the side area (2) is less than in commercially available mask beads and is in the range of 6-14 mm, preferably 8.4 mm. It will also be noted how the wall thickness in the side area decreases continuously from the base (W2) toward the bearing area (W4).

FIG. 2C shows the bead sectioned in the plane z. It can be clearly seen here that the nose bridge area (1) is recessed.

In FIG. 3, the differences between the mask bead (M) according to the invention and mask beads from the prior art (M') and (M") are shown clearly in a perspective view. In particular, it can be clearly seen that the nose bridge area (1) is higher than the nose bridge areas (1' and 1").

Figure 4:
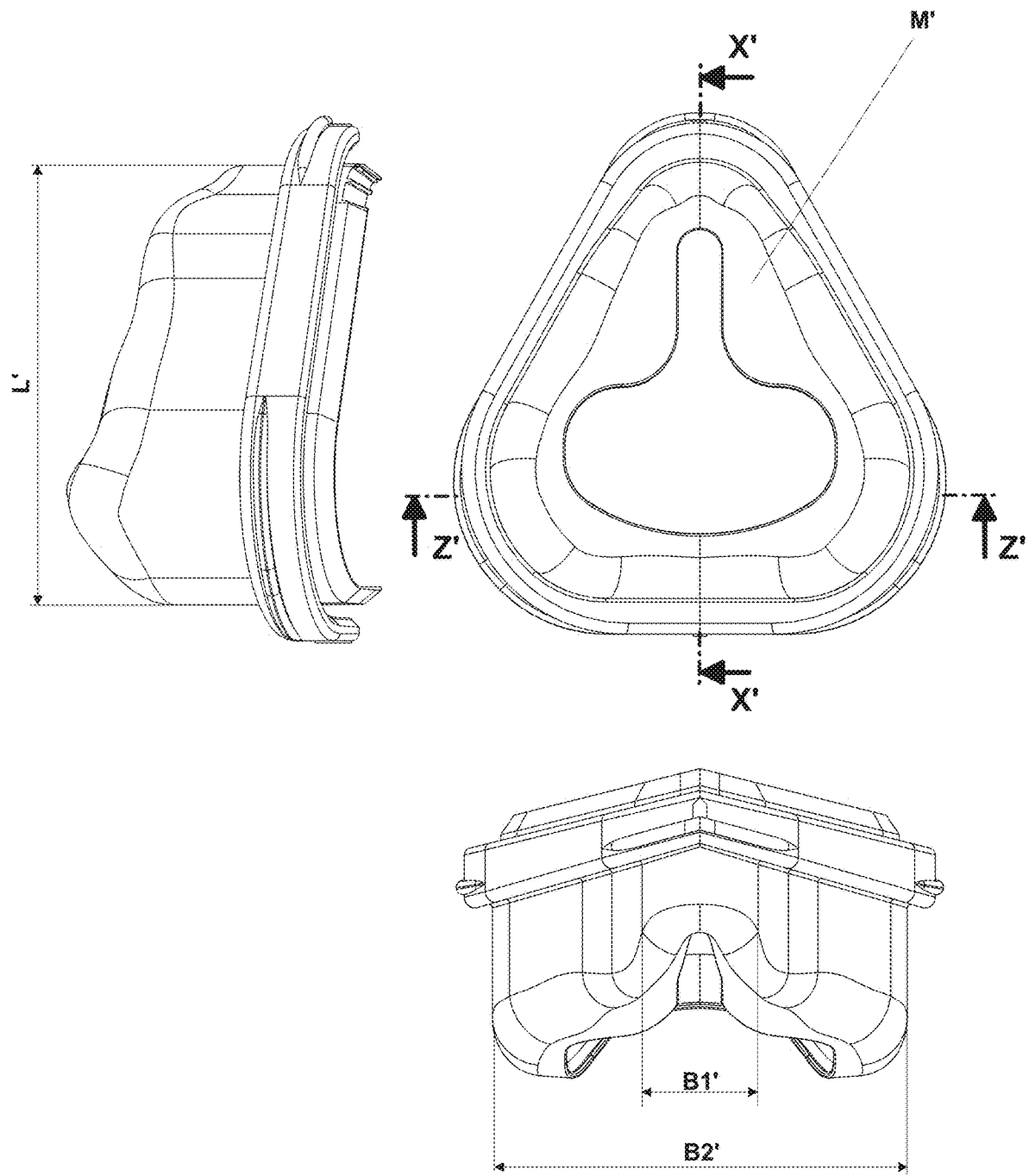
FIG. 4 shows the mask bead (M') in different views
Figure 6:
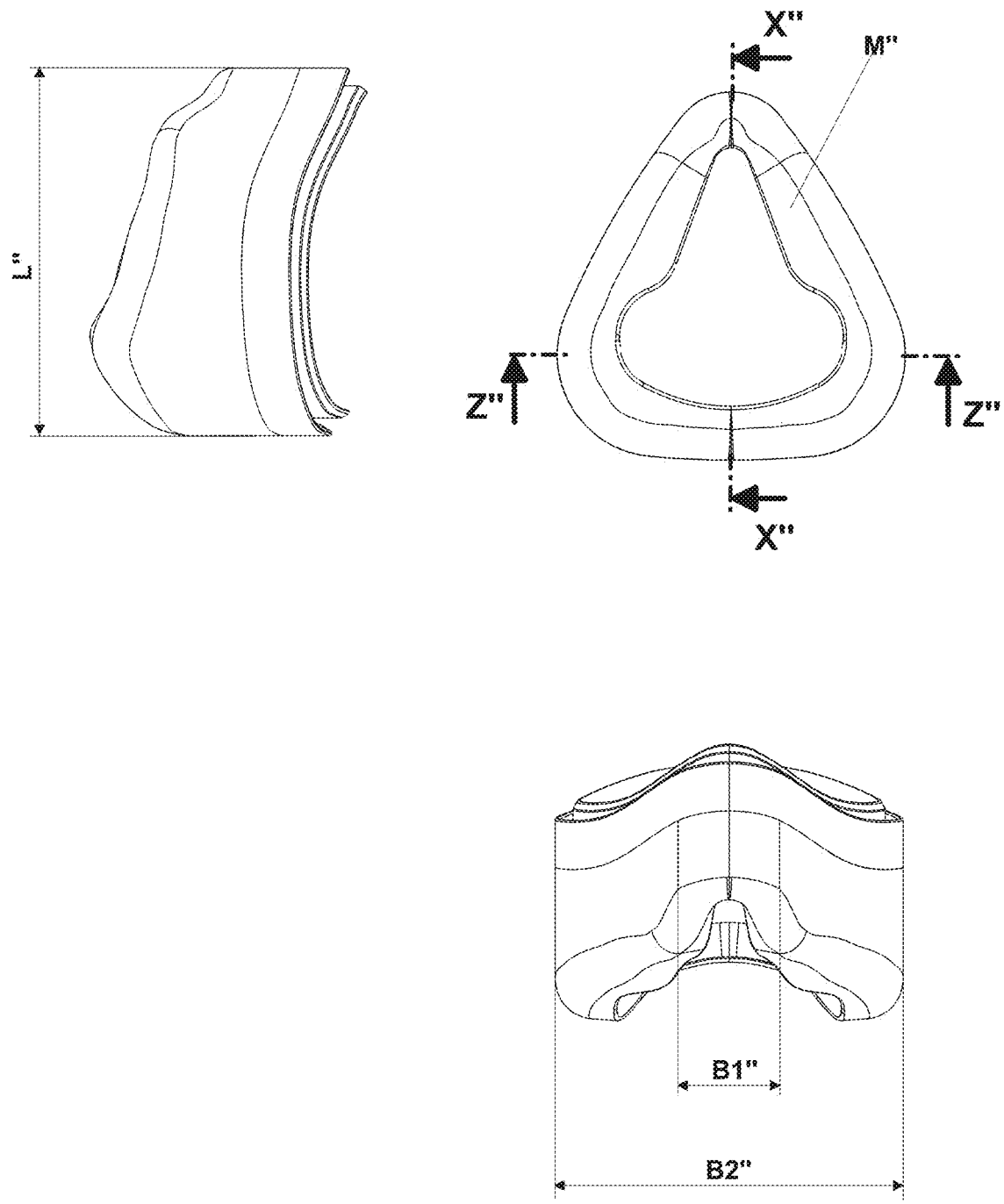
FIG. 6 shows the mask bead (M") in different views

FIGS. 4 and 5 show a mask bead (W), and FIGS. 6 and 7 show another mask bead (M") from the prior art.

Comparing the mass of the mask bead (M) to the masses of the mask beads (M' and M") makes clear the difference between the invention and the prior art.

A feature of the mask bead (M) according to the invention is the very great range of deformation of the nose bridge area (1), which is achieved by the suitable choice of the wall thickness (W1), of the width (B1) and of the first height (H1) and the further height (H4). This range is important for the adaptability to different sizes and different shapes of nose parts of the patients.

The width (B2) is the maximum width of the mask bead measured at the outer edges of the side areas (2) in the area next to the contact point (5) to the mask body. The width (B2) is alternatively the maximum width of the contact area.

The length (L) is the maximum length of the mask bead measured in the plane of symmetry of the mask between the nose bridge area and upper lip area.

The adaptability to different sizes and different shapes of nose parts of the patients is manifested in particular in the special design of the nose bridge area. From the comparison between the invention and the prior art (see FIGS. 3 to 7), it is clear that, in the bead according to the invention, it is not only the ratio B1 to B2 that differs from the prior art, but also the ratio H1 to H2. According to the invention, H1 is always the same as or greater than H2. In masks from the prior art, H1 is always smaller than H2.

The length (L) is preferably 58 mm and is shorter compared to the lengths (L') of 61.5 mm and (L") of 62.5 mm.

The width (B2, B2' and B2") is the same in all three beads and is in the range of 59 mm, whereas the width of the nose bridge area (B1) in relation to the widths (B1') and (B1") is twice as wide and according to the invention lies in the range of 33.7 mm. The wall thickness (W1) is half as thick as the wall thicknesses (W1') and (W1") and lies in the range of between 0.25 mm and 0.5 mm. The height (H1) is in the range of 18-27 mm, here 22.2 mm, and is approximately 1.4 to 2.1 times greater than the heights H1'=12.7 mm and H1"=15.2 mm.

The height (H2) of the side areas (2) is only about 0.6 times the heights (H2' and H2"). The height (H3) of the chin area (3) is about 0.7 times the heights (H3' and H3") and is therefore less than in commercially available mask beads.

The height (H7) (difference between the nose bridge bearing and the bearing in the side area) is approximately the same as the heights (H7' and H7").

To achieve a high degree of adaptability to different sizes and different shapes of nose parts of a patient, the mask bead has, in the nose bridge area, a very broad form (B1) with a very large, thin-walled area that is easily deformable. In this area, which makes up about ⅓ of the periphery, the mask bead has a wall thickness of ≤0.6 mm and, in this area, it is also about twice as high as in the side areas of the bead. However, in order to avoid an inward kinking of this area when pressure is applied to the area, an arc-shaped contour was chosen from the contact area toward the bearing surface in the nose bridge area.

The invention is suitable in particular for masks that cover only the nose of the user, although good results were also obtained with full-face masks according to the invention that cover the mouth and nose of the user.

The mask bead has an area suitable for applying an identification marking. The area is preferably in the upper lip area. This can be printed or lasered or engraved, for example.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A mask bead for a patient interface, wherein the mask bead comprises a contact area, a nose bridge area having a width (B1), side areas, a base area, and a bearing area on a patient, the bearing area extending from the side areas and the base area and the nose bridge area to a central opening and being designed as a sealing lip which frames the central opening that serves at least for introduction of a nose of the patient, and wherein a wall thickness (W1) in the nose bridge area is ≤0.6 mm and the mask bead has a maximum width (B2), a ratio B1 to B2 being one to three or greater.

2. The mask bead of claim 1, wherein the wall thickness (W1) is 0.25-0.5 mm.

3. The mask bead of claim 2, wherein a height (H1) in the nose bridge area is 20-25 mm.

4. The mask bead of claim 1, wherein the nose bridge area has a width (B1) of 27-37 mm.

5. The mask bead of claim 1, wherein a height (H1) in the nose bridge area is 17-27 mm.

6. The mask bead of claim 1, wherein a height (H4) in the nose bridge area is 14-23 mm.

7. The mask bead of claim 1, wherein the nose bridge area has an arc-shaped contour (R).

8. The mask bead of claim 1, wherein the base area has a wall thickness (W3) of 0.8-1.2 mm and/or a side area has a wall thickness (W2) of 1.5-2.8 mm.

9. The mask bead of claim 1, wherein a height (H3) of the base area is 16-21 mm and/or a height (H6) of the base area is 8.5-13.5 mm.

10. The mask bead of claim 1, wherein a height (H2) of a side area is 12-22 mm.

11. The mask bead of claim 10, wherein the height (H2) of a side area is 14-16 mm.

12. The mask bead of claim 1, wherein a height (H5) of a side area is 6-14 mm.

13. The mask bead of claim 1, wherein a wall thickness in a side area decreases continuously from a base (W2) toward a bearing area (W4).

14. The mask bead of claim 1, wherein the bearing area has an approximately constant wall thickness (W4) in a range of 0.2-0.75 mm.

15. The mask bead of claim 1, wherein a ratio of a length (L) of the mask bead to a width (B2) is approximately 1 to 1.

16. The mask bead of claim 1, wherein a width (B2) is approximately in a range of from 50 mm to 65 mm.

17. The mask bead of claim 16, wherein the width (B2) is approximately in a range of from 54 mm to 63 mm.

18. The mask bead of claim 1, wherein a height (H1) in the nose bridge area is always the same as or greater than a height (H2) of a side area.

19. The mask bead of claim 1, wherein the mask has a length (L) in a range of from 50 mm to 65 mm and a width (B2) in a range of from 50 mm to 63 mm.

20. The mask bead of claim 19, wherein the mask has a length (L) in a range of from 53 mm to 62 mm and a width (B2) in a range of from 53 mm to 63 mm.

* * * * *